United States Patent [19]

Nohl et al.

[11] Patent Number: 4,823,622

[45] Date of Patent: Apr. 25, 1989

[54] SAMPLE METERING VALVE FOR A SAMPLE PREPARATION SYSTEM

[75] Inventors: Andre J. Nohl, Menlo Park; Vance J. Nau, Cupertino, both of Calif.; Andre Metzger, Le Verger, France

[73] Assignee: Spectra Physics, San Jose, Calif.

[21] Appl. No.: 942,201

[22] Filed: Dec. 16, 1986

[51] Int. Cl.⁴ .............................................. G01N 1/14
[52] U.S. Cl. ............................... 73/863.71; 73/864.22
[58] Field of Search ........... 73/863.71, 863.72, 863.73, 73/863.83, 863.01, 863.31, 863.32, 863.33, 864.21, 864.34, 864.35, 864.73, 864.22; 422/100

[56] References Cited

U.S. PATENT DOCUMENTS

| | | | |
|---|---|---|---|
| 2,434,723 | 1/1948 | Shook | 73/863.71 |
| 3,638,498 | 2/1972 | Nelms | 73/863.71 |
| 3,981,179 | 9/1976 | Roof | 73/61.1 C |
| 4,002,053 | 1/1977 | Hayakawa | 73/32 R |
| 4,117,727 | 10/1978 | Friswell et al. | 73/864.21 |
| 4,181,009 | 1/1980 | Williamson | 73/61.4 |
| 4,194,398 | 3/1980 | Gastrock | 73/863.71 |
| 4,433,587 | 2/1984 | Risdal | 73/863.54 |
| 4,441,374 | 4/1984 | Suzuki | 73/864.21 |
| 4,445,391 | 5/1984 | Cabrera | 73/864.12 |

FOREIGN PATENT DOCUMENTS

| | | |
|---|---|---|
| 1914118 | 3/1969 | Fed. Rep. of Germany. |
| 3346196 | 7/1985 | Fed. Rep. of Germany. |
| 1376755 | 9/1964 | France. |
| 2076797 | 9/1971 | France. |
| 544302 | 11/1973 | Switzerland. |
| 1174469 | 4/1968 | United Kingdom. |

OTHER PUBLICATIONS

Altermatt et al., (1986) "Messen Von Stoffspezifeschen Groben In Der Chemischen Produktion-Erfahrungen, Trends."

Primary Examiner—Stewart J. Levy
Assistant Examiner—Robert R. Raevis
Attorney, Agent, or Firm—Paul Davis; Ron Fish

[57] ABSTRACT

A sample metering valve for both liquid samples and slurry samples with entrained gas bubbles. The sample metering valve for liquids is comprised of a piston with sample chambers formed in the side thereof said piston moving freely into and out of a cylinder having an aperture matching the size of the piston. Sealing is provided by a seal which has no dead volume which cold flows under a spring bias to maintain the seal under various operating conditions. The sample metering valve for slurry samples includes a syringe embodiment having separately moving piston and valve in a cylinder. The syringe valve sucks up sample with a piston, isolates the sample with the valve and compresses the entrained gas bubbles with the piston. Another embodiment uses three, three way valves which are coupled to a pump and a means to compress the sample. The valves are operated to suck a portion of sample up into the tubes connecting the valves, isolate the sample from the sample container, compress the sample using the compressed gas and trap a known volume of the compressed sample in the tube between valves. The trapped sample is then flushed out of the system with diluent to prepare the sample for analysis.

3 Claims, 3 Drawing Sheets

SAMPLE METERING VALVE FOR A SAMPLE PREPARATION SYSTEM

BACKGROUND OF THE INVENTION

The invention relates to the field of sample preparation for performing chemical assays. More particularly, the invention relates to the field of sample metering valves for extracting a known volume of a sample out of sample containing chamber or a process stream of materials to be assayed.

Typically in chemical processing facilities and chemical analysis labs it is desirable to perform chemical assays. Often this analysis is done by liquid or gas chromatography, although many other methods of assaying samples for their chemical composition also exist. Often, before an assay can be done it is necessary to prepare the sample by isolating a known volume of the sample from a container of same or by isolating a known volume of the sample from a process stream. The portion of the sample so isolated is then diluted by adding the isolated sample volume to a known quantity of diluent to prepare a sample solution of a user defined concentration for the assay.

The amount of sample so isolated must generally be a precisely known volume so that the concentration of the final sample solution can be precisely controlled. There is a prior art valve which has been used to perform this function which is manufactured under the trademark ISOLOK by Bristol Engineering Company of Yorkville, Ill. This valve uses a T shaped end on a piston within a cylinder. The cylinder is open ended and the piston's T shaped end forms a cap on the cylinder when the piston is in the retracted position. When the piston is in the extended position, the end cap of the piston is moved away from the end of the cylinder. The piston has a cylindrical shaped recess therein which is formed a distance up from the distal end of the piston. When the piston is driven to the extended position, the recess is pushed out of the cylinder into the surrounding environment and fills with whatever medium surrounds the valve. The user of the ISOLOK valve takes a sample by causing the piston to extend out into the surrounding environment such that the recess fills with the material which surrounds the valve. Typically, the piston is driven to the extended position by a pneumatic drive arrangement or by a stepper motor. After the recess is filled, the driving apparatus retracts the piston back into the confines of the cylinder. This causes the end cap of the piston to seal the end of the cylinder so that no material outside the walls of the cylinder can get into the cylinder or the recess thereby isolating a known volume of sample material in the recess.

The problem with the ISOLOK valve is in the sealing arrangement. Three O ring seals are used around the circumference of the piston both above and below the recess. These O rings are separated by small spaces, and engage the side walls of the cylinder in sealing engagement. The gaps between the O rings are themselves small recesses, and the gaps around the portion of the piston below the recess are exposed to the surrounding medium when the piston is in the extended position. Because of this fact, the gaps between the O rings around the portion of the piston which is exposed fill with the medium which fills the main sample isolation recess when the piston is put into the extended position. When the piston is retracted into the cylinder, the material trapped between the O rings effectively is part of the isolated sample and is of unknown volume. If the isolated sample is then diluted by extending the piston again into a known volume of diluent, the isolated sample is released into the diluent along with whatever sample is trapped between the O rings. The result that instead of a known concentration of sample in diluent, there is an unknown concentration of sample in the diluent. Further, the inaccuracy of the sample volume is not a constant deviation. There are variations in the error which occur often enough that the predictability of the error is low. This can degrade the precision of the assay.

The ISOLOK valve also is not well suited to dealing effectively with slurries or liquid samples with entrained gas bubbles. The gas bubbles take up volume which could otherwise be filled with liquid and thereby decrease the accuracy of prediction of the exact amount of liquid sample which has been isolated.

Thus a need has arisen for a valve which can accurately and repeatedly isolate a known volume of a sample from a larger volume stored in a container or from a process stream and which can handle the situation of entrained gas bubbles or foam in the sample chamber or process stream gracefully and with precision.

SUMMARY OF THE INVENTION

According to the teachings of the invention, there is disclosed herein a sample metering valve which can repeatedly and accurately isolate a known volume of sample from a larger volume of sample. The sample metering valve of the invention includes an open end cylinder in which there is positioned a piston having a T shaped end. The piston slides back and forth in the cylinder between an extended position and a retracted position. The T shaped end is sized so as to form a sealing plug in the open end of the cylinder. A cylindrical recess is formed in the piston up from the sealing plug end and is placed on the piston such that the recess is exposed to the surrounding medium when the piston is in the extended position. This causes the recess to fill up with the material of the surrounded medium when the piston is extended. When the piston is retracted, the material in the recess is isolated.

No O ring seals are used on the piston in the valve of the invention. Instead, there are two rings of relatively harder, less deformable material affixed to the walls of the cylinder in sealing engagement with the side walls of the piston. These two rings are separated by a cylinder of relatively softer, more deformable material such that the two rings of relatively harder material are in contact with the end surfaces of the softer material. A spring is disposed inside the cylinder concentrically around the piston. This spring contacts the ring of relatively harder material at the end of the softer material farthest from the sealing plug on the piston. The purpose of the spring is to apply a bias force to the relatively harder ring to exert pressure on the softer material to cause it to expand against the side wall of the piston thereby forming a better seal. Because there are no gaps between the relatively harder sealing rings and the relatively softer sealing cylinder, and because the intersections between the rings are not exposed to the surrounding medium when the piston is extended, no dead volume is available to fill with unknown volumes of sample.

Typically, the piston is driven either by a pneumatic system or by stepper motors.

Another embodiment of a metering sample valve is a syringe type valve. This valve is especially useful in dealing with slurries with entrained gas bubbles or foam. These bubbles of gas take up volume in an isolated sample which can lead to inaccuracy in predicting the actual volume of liquid which has been isolated in a metering valve. The syringe tube sample metering valve utilizes a cylinder with a piston therein and a separately movable end plug. The end plug is moved to an open position so that the surrounding medium may enter the cylinder. During filling of the valve, the piston is left in its retracted position to leave maximum volume inside the cylinder available for filling by the sample. After the cylinder sample volume is filled, the piston is separately moved down toward the sealing end plug thereby compressing any gas bubbles entrained in or otherwise trapped in the sample volume of the cylinder. During this downward movement of the piston, the amount of movement is monitored by a sensor. When the piston will move no more, the total movement is determined from the sensor or by reading the motor step number in the case of a stepper motor drive for the piston. The total volume of liquid in the syringe valve is calculated by subtracting the volume displaced by the movement of the piston from the total original volume of sample in the cylinder before the movement of the piston.

The sample may then be released by causing the end plug to unseal the cylinder and either letting the sample flow out or by pushing it out by further movement of the piston. With liquid samples, especially very viscous samples, the syringe type embodiment has the added advantage that the process of filling the cylinder sample volume with sample may be speeded up by using the piston to draw up the sample into the cylinder by moving it away from the sealing plug from a position adjacent to the sealing plug at the time the plug is opened.

The preferred embodiment of the sample metering valve for use in slurry and other sample situations where the volume consumed by gas bubbles exists is comprised of three, three way valves coupled to a sample pumping mechanism and a means to exert force on the sample to cause it to compress. A first three way valve (basically a Y valve) has its common port coupled to a fill pipe in a sample chamber, and a number 1 port coupled to the number 1 port of another three way valve. This connection forms a sample chamber between the valve mechanisms of the first and second valves. The number 2 ports of the two valves are coupled together to form a bypass loop. The common port of the number 2 valve is coupled to the common port of a third three way valve which has one of its ports coupled to the sample pump and the other port coupled to the source of pressurized gas.

The valves are operated to couple the sampling pump to the fill tube into the chamber and the sample pump is driven to suck sample up through the first valve and out through the sample chamber until enough sample is drawn to completely fill the sample chamber and excess sample is drawn to account for the effects of compression. The first valve number 1 port is then closed to isolate the sample in the sample chamber, and the third valve is operated to couple the pressurized gas into the sample chamber to compress the gas bubbles in the sample to a small volume. Any means of comrpession will do. This includes operating the pump in reverse. The second valve is then operated to trap the compressed sample between the first and second valving mechanisms, which is a known volume. The sample pump is then used to empty the rest of the sample not so trapped from the lines and from the sample chamber and to clean out the lines and the sample chamber with solvent. The valves and pump are then operated to free the trapped sample and to pump a known quantity of solvent through the lines and to push the trapped sample into the sample chamber where it may be pumped to any analysis device.

DETAILED DESCRIPTION OF THE PREFERRED EMBODIMENT

Figure 1:
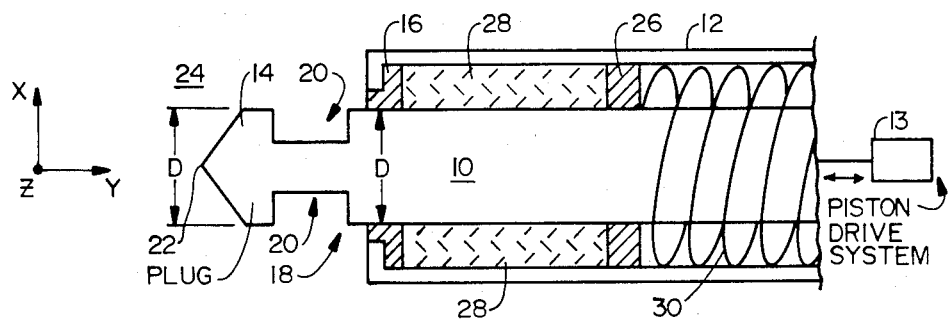
FIG. 1 is a cross sectional view of the sample metering valve of one embodiment with the piston in the extended position.
Figure 2:
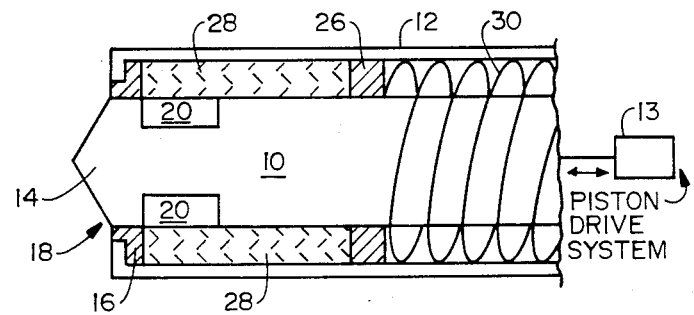
FIG. 2 is a cross sectional view of the sample metering valve of the embodiment of FIG. 1 with the piston in the retracted position.

Referring to FIG. 1, there is shown a cross sectional view of the sample metering valve of the preferred embodiment. A piston 10 is disposed within an open ended cylinder 12. The piston is typically metal with a chrome finish or is highly polished so as to have a smooth surface to minimize friction as the piston moves back and forth on the y axis. The piston has a T shaped end with a sealing plug 14 which has the same outside diameter D as the inside diameter of a seal 16 at the "open" end 18 of the cylinder. The piston 10 is shown in the extended position. In the retracted position of the piston 10, shown in FIG. 2, the sealing plug 14 is pulled back into the opening in the cylinder 12 so as to be in sealing contact with the sealing ring 16.

The piston 10 has a sample collecting recess 20 formed therein a small distance along the y axis away from the tip 22 of the piston. The purpose of the sample collecting recess 20 is to capture a known volume of material from the surrounding medium 24 when the piston is in the extended position. Therefore, the recess 20 must be machined or otherwise formed to be of a known volume and must be placed on the piston 10 and sized so as to be at least partially exposed to the surrounding medium 24. Preferably, the recess 20 will be placed and sized so as to be completely exposed to the surrounding medium 24 when the piston is in the extended position as shown in FIG. 1. The piston may be formed of other materials than metal such as teflon or other plastic materials. This is true of the cylinder 12 also. The caveat on material selection is that the materials selected for any component of the valve must be compatible with the intended environment in which the valve is to be used so that the environment will not adversely affect the materials and cause a valve failure. This is particularly true in sampling of process streams.

A significant improvement over the prior art for the valve of FIG. 1 resides in the sealing structure. This structure has no dead volume or recesses which can inadvertently collect unknown volumes of sample when the piston is in the extended position. This is accomplished by the elimination of multiple O rings for sealing and substitution of a flexible, self compensating sealing arrangement using the property of cold flow of malleable materials to adjust for differences in dimensions of the various components with variations in temperature. The sealing structure is comprised of two sealing rings 16 and 26 of relatively harder materials with a smaller creep rate (non recoverable strain or permanent pecentage deformation or cold flow) separated by and in abutting contact with a cylindrical seal 28 of malleable material of a relatively faster creep rate. A spring 30 applies a constant force to the upper sealing ring 26 biasing it to move toward the sealing ring 16 thereby putting the sealing cylinder 28 in compression stress. This causes the cylindrical seal 28 to attempt to cold flow, i.e., expand in whatever direction is available for expansion in response to the compression stress. If there is any gap between the sidewalls of the piston 10 and the cylindrical seal 28, the cold flow results in radial strain in the cylindrical seal 28 which reduces or eliminates the gap thereby effecting a good seal. Changes in temperature which alter the diameters of the piston 10 and the cylinder 12 (possibly differentially) will not adversely affect the integrity of the seal. This follows because the cold flow strain adjusts for any temperature induced changes in gap size since the pressure exerted by the spring 30 is substantially constant regardless of changes in temperature. Substantially less cold flow in the sealing rings 16 and 26 results because of their relatively harder constitution.

No dead space results in the sealing structure of the invention since there are no gaps between the sealing rings 16 and 26 and the cylindrical seal 28. Further, the seals are affixed to the cylinder and not to the piston, so the seals never are moved by the piston out into the surrounding medium. No spurious, unknown quantities of sample can be accumulated by the seals because of this structure.

The apparatus to move the piston may be any known force producing apparatus such as pneumatic or electrical devices. It is not necessary in the preferred embodiment to know exactly how far the piston moves since the sample volume is fixed in the recess 20. It is only necessary to know that the piston has been moved to its extended position or to its retracted position.

In the preferred embodiment, the sealing rings 16 and 26 are teflon impregnated with glass, graphite or some other material which makes the TEFLON alloy harder than pure TEFLON POLYMER. The sealing cylinder 28 is pure TEFLON POLYMER and has a higher degree of deformability than the sealing rings 16 and 26. These material selections are not critical to the invention however, and any material which is chemically inert, has a low coefficient of friction and which can cold flow will be acceptable for the sealing cylinder 28. The same is true for the material selection of the sealing rings 16 and 26 except that the material must be relatively less deformable than the sealing cylinder 28, or must be capable of being made so with suitable alloying or other techniques.

Syringe Valve

Figure 3:
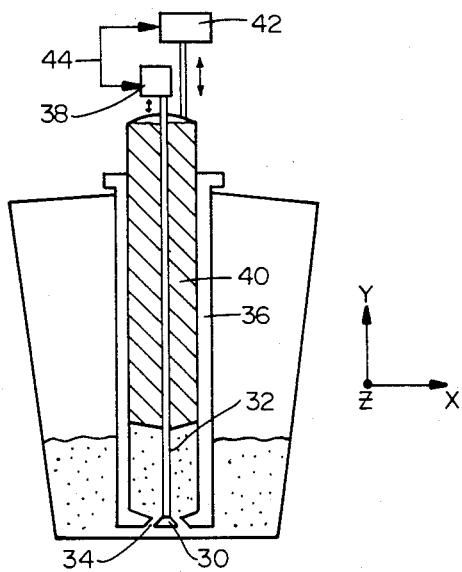
FIG. 3 is cross sectional view of the syringe type sample metering valve.

Referring to FIG. 3 there is shown a cross section of a syringe type sampling valve which is advantageous for use in sampling slurry type samples and samples with entrained gas bubbles or surface foam bubbles which take up space. The syringe type valve is comprised of two separately movable sections. A valve 30 driven by a shaft 32 opens and closes a port 34 in a cylindrical valve body 36. The valve is driven into and out of sealing engagement with a valve seat formed on the port 34 by a valve drive system 38 of known construction. The details of the valve drive system 38 are not critical to the invention, and any mechanism which is capable of causing the valve 30 to move into and out of sealing engagement with the valve body 36 will suffice for purposes of practicing the invention.

The other portion of the sample valve which moves independently is the piston 40. The piston 40 moves back and forth inside the body 36 of the valve along the y axis under the influence of a piston drive system 42. The piston 40 has a hole therein through which the shaft 32 of the valve 30 passes. The clearance between the shaft 32 and the walls of the hole in the piston 40 should be such that substantial sealing engagement between the shaft and the walls of the hole in the piston is maintained. This necessary because the piston 40 will be forced downward in the negative y direction to compress any gas in the sample to minimal volume, and pressure will result in the chamber which could escape around the valve shaft 32 unless a sealing fit is maintained. Because of this sealing engagement, the materials selected for the valve shaft 32 and the piston 40 should not only be able to withstand the forces involved, but should also have low coefficients of friction.

The details of the piston drive mechanism are not critical to the invention except that the piston drive mechanism 42 should be such that the amount of movement of the piston 40 can be accurately determined during the compression stage of operation of the sampling valve. A stepper motor system or a motor system or pneumatic system coupled with an optical or other type of sensor which can accurately determine the amount of movement of the piston 40 will suffice for purposes of practicing the invention. Any type of motive power source which can move the piston 40 will suffice, and any type of sensor or other device which can detect and signal the amount of movement of the piston 40 will suffice for purposes of practicing the invention.

Because the piston drive system 42 and the valve drive system must work together in a coordinated fashion to process samples with gas bubbles which must be compressed, a communication link or control bus 44 is shown to carry the proper signals from one unit to the other to allow the needed cooperation to occur.

Referring to FIGS. 4 through 7 there are shown a sequence of states of the two moving parts of the syringe to take a sample, compress the gas volume to a small volume and measure the sample volume after compression and to release the sample.

Figure 4:
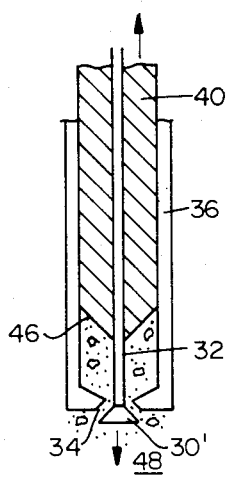
FIG. 4 is a cross sectional view of the state of the syringe type sample metering valve as an aliquot of sample is drawn up into the valve.

FIG. 4 shows the state of the syringe valve as it is filled with sample. In this state, the valve operation mechanism 38 forces the valve 30 open by pushing the valve shaft 32 downward in the negative y direction. Simultaneously or after the valve 30 is unseated, and the aperture 34 is opened, the piston 40 is pulled upward in the positive y direction by the piston drive mechanism 42. This increases the volume of the "chamber" defined by the end 46 of the piston, the inside walls of the cylinder 36 and the end of the cylinder 36 having the aperture 34. The resultant lowering of pressure causes the sample slurry 48 to be sucked up into the chamber of the syringe valve.

Figure 5:
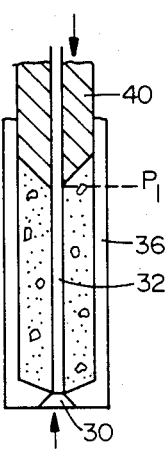
FIG. 5 shows the state of the syringe type sample metering valve as the aliquot of sample is compressed to reduce the volume consumed by the gas bubbles.

Referring to FIG. 5 there is shown the state of the syringe valve as the entrapped gas bubbles are compressed. The piston 40 is shown at its fully retracted position. The valve control mechanism 38 has closed the valve 30 to block any flow of sample into or out of the sample chamber by pulling the valve shaft 32 upward in the positive y direction. The piston drive mechanism 42 then pushes the piston 40 downward in the negative y direction to begin compressing the gas bubbles in the sample. The piston drive mechanism 40 must be such that the position of the piston 40 in its retracted position $P_1$ can be noted so that the total movement of the piston downward in the negative y direction may be calculated. The total travel of the piston 40 during the compression must be capable of accurate measurement by the piston drive mechanism 42. Typically, a stepper motor system would be used for the piston drive mechanism 42 with a computer acting through a motor controller interface chip controlling the motor. To implement the movement of the piston along the positive y direction, the computer sends a motor movement command to the motor control interface chip (not shown) in the piston drive control mechanism 42. Typically, this command would include the number of steps to move or the step address for the position $P_1$ with a command to start moving in the positive y direction and to stop moving when the designated step address is reached for the position $P_1$. Alternatively, the computer can send a command to start moving in the positive y direction and then continually query the motor control interface chip to read the current step number as the movement progresses. As the data is received from the motor controller interface chip, the current step number is compared with the desired step number, and a stop command is issued to the motor controller chip when the piston reaches step $P_1$. All such embodiments would be equivalent. Alternatively, simpler pneumatic equipment may be used to move the piston 40 between upper and lower stops with the upper stop being the position $P_1$, and the lower stop being the bottom of the cylinder 36. To start the piston moving downward as in FIG. 5, the computer would issue a start command and direction data to the motor controller interface chip to cause the piston to move in the negative y direction. This movement would continue until all the gas bubbles were compressed. A detector mechanism to detect the amount of "backpressure" on the piston may be used to determine when the amount of back pressure is sufficient to indicate that all the gas bubbles have been compressed sufficiently. What is a sufficient amount of compression must be determined by the user, and will depend upon the level of accuracy in the final diluted sample concentration desired. For very accurate sample concentrations, more compression is used to insure the final volume of the chamber is substantially all sample liquid.

Figure 6:
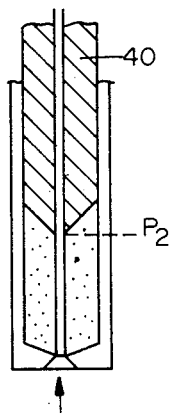
FIG. 6 shows the state of the syringe type valve after the piston has reached the point where the gas in the sample has been substantially compressed.

Referring to FIG. 6, there is shown the state of the syringe sample valve after the compression is done. The piston 40 is shown in its final position after sufficient compression of the gas bubbles in the sample liquid has occurred. The valve 30 is left closed during the compression stroke by the piston 40. The operation of the piston drive mechanism 40 to achieve the state shown in FIG. 6 depends upon the type of piston drive mechanism 42 which is used. As mentioned above, the particular design for the piston drive mechanism 42 is not critical to the invention as long as the criteria stated above can be met. Those skilled in the art will appreciate many different mechanisms which could be used for the piston drive mechanism 42. The same is true for the valve control mechanism 38. The design for computer controlled stepper motor systems and the programming for same is well understood by those skilled in the art. For a computer controlled stepper motor system, the movement of the compression stroke could be accomplished as follows. When a sufficient amount of back pressure is detected or adequate compression is otherwise detected, the computer issues a stop command to the motor controller interface chip, and the piston stops at the position $P_2$. The computer then reads the step number for the current piston position. This step number is compared to the step number for the position $P_1$, and the difference is then converted into the distance of travel for the piston along the y axis from position $P_1$ to position $P_2$. This distance may then be converted to the final volume of the sample shown in FIG. 6. This is done by calculating the volume difference between the volume at position $P_1$ and the volume at position $P_2$ using the amount of linear piston travel between these positions.

In other embodiments, the valve controller 38 is programmed or otherwise constructed to apply a certain, user defined force to the valve 30 to keep it closed. The piston controller 42 is then programmed to apply downward pressure to the liquid in the sample chamber until the pressure in the liquid is enough to force the valve open. This valve opening event is detected by sensing movement of the valve shaft 32 or by detecting fluid escaping from the sample chamber optically or otherwise. The amount of compression can be controlled in this embodiment by controlling the amount of force applied to keep the valve 30 closed. The time of the valve opening is signaled to the controller by an interrupt from whatever sensor (not shown) is used to detect the opening of the valve 30. This allows the controller to either stop moving the piston 40 or to continue using the piston until the volume of liquid in the sample chamber is the user defined amount. This final volume may be determined by continual query to the stepper motor controller to determine the current step position and comparison to the step number calculated for the volume desired by the user.

In still other alternative embodiments, the user may program the piston 40 to move to a position $P_1$ which represents a predetermined volume differential over the volume represented by position $P_2$. The volume represented by position $P_1$ will be greater than the volume represented by position $P_2$ by an amount determined by the user from the characteristics of the slurry or other sample being used. That is, the user will, for a given type of sample, know the approximate volume of the gas in the sample which must be compressed. This embodiment assumes that all samples contain the same volume of gas represented by the volume differential between positions $P_1$ and $P_2$.

Those skilled in the art will appreciate other embodiments for or ways of operating the piston controller 42 and the valve controller 38 to accomplish the gas compression in moving the piston from the position $P_1$ to the position $P_2$. As long as these other embodiments are capable of compressing the gas so that the final volume of liquid in the sample chamber shown in FIG. 6 is substantially all liquid, then these embodiments are regarded as equivalents.

Figure 7:
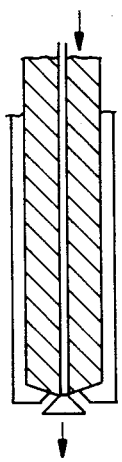
FIG. 7 shows the state of the syringe type valve after the valve has been opened and the piston has been pushed down to the end of the cylinder to push out the sample liquid.

FIG. 7 shows the final stage of the slurry sampling process after the sample liquid in the sample chamber of FIG. 6 has been pushed out of the valve. To accomplish this, the valve controller 38 pushes the valve 30 open in any known fashion, and the piston controller 42 pushes the piston 40 down the negative y axis until the piston 42 reaches the valve seat end of the cylinder 36.

Figure 8:
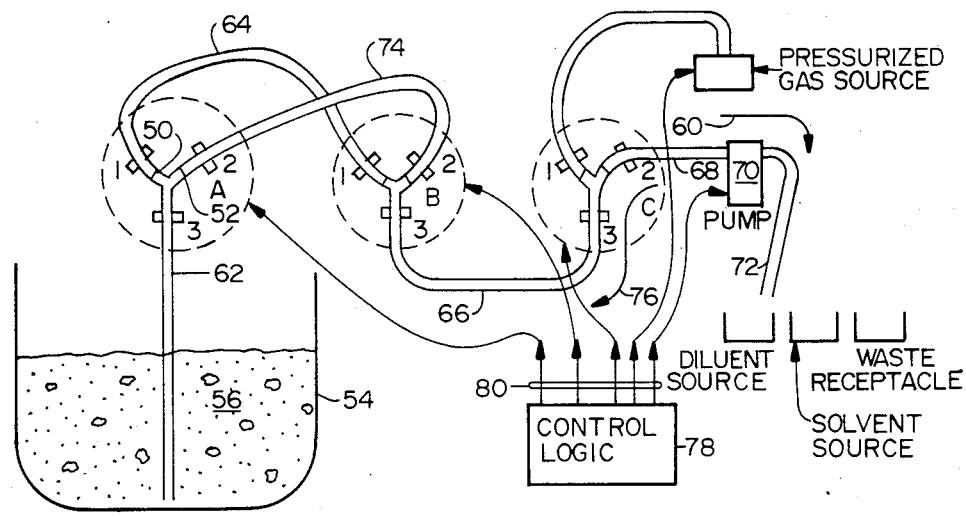
FIG. 8 is a diagram of the preferred embodiment of the sample metering valve.

FIG. 8 shows the preferred embodiment of the sample metering valve for slurry or other samples where the volume consumed by gas bubbles is to be eliminated or minimized. The sample metering valve is actually comprised of three, three way valves labelled A, B and C in FIG. 8. Each three way valve is a Y connection with a valve gate such as the gates 50 and 52 in valve A, and each valve A through C has three ports labelled 1 through 3. The gate valves in each valve operate so that at any particular time only one of ports 1 or 2 is coupled to port 3. The connections are as shown in FIG. 8 for the sample metering valve of the preferred embodiment.

The operation of the system to take a sample is as follows. A sample cup 54 is filled with sample 56. Ports 1 on valves A and B are then activated (opened), and port 2 of valve C is activated. A sample pump coupled to port 2 of valve C is then turned on to pump liquid in the direction of arrow 60. This draws sample up into the fill tube 62 and through ports 3 and 1 of valve A, pipe 64, ports 1 and 3 of valve B, pipe 66, ports 3 and 2 of valve C, pipe 68, pump 70 and empty pipe 72. Any pumping mechanism or system will suffice for practicing the invention as long as the accuracy of delivery at least in the direction of flow into the sample cup 54 can be controlled. An accurate pump is needed for dilution, but is not needed for sample isolation.

The pump 70 must be pumped long enough to completely fill the pipe 64 and at least partially fill pipe 66 with enough sample such that when the sample is compressed, the pipe 64 remains filled to capacity. The sample chamber of known volume in the embodiment of FIG. 8 is the pipe 64 plus whatever volume exists in the valves A and B up to the valve plates.

After filling the sample chamber, valve A, port 2 is activated to trap the sample in the pipe 64, and valve C, port 1 is activated to couple pressurized gas into pipe 66. This pressurizes the liquid and gas in the pipes 66 and 64 and thereby compresses any gas bubbles in the pipes 64 and 66 down to zero or small volume. The volume of material in the sample chamber is substantially all liquid by virtue of this pressurization of the lines. Next, valve B, port 2 is activated thereby isolating the sample in the sample chamber 64 between valves A and B. The pump 70 is then activated to pump the remaining sample 56 in the sample cup and any remaining untrapped sample in pipe 66 out of the system through pipe 72. That is, sample is pumped up through fill pipe 62, ports 3 and 2 of valve A, pipe 74, ports 2 and 3 of sample valve B, pipe 66, ports 3 and 2 of valve C, pipe 68, pump 70 and out pipe 72.

Pipe 72 in the preferred embodiment may be coupled alternately to a source of solvent and to a waste dump. The pump 70 is then activated to pump solvent in the direction of the arrow 76 to flush out the pipes 66, 74 and 62 and to wash out the remaining sample from the sample cup 54. The pump 70 is then reversed to pump out the solvent in the system and the sample cup in preparation for the dilution.

Next, ports 1 of valves A and B are activated, and the pump 70 is activated to pump in the desired amount of diluent to get the desired sample to diluent concentration. The diluent pumped in the direction of the arrow 76 flushes the trapped sample out of the pipe 64 down into the sample cup 54. Since the volume of trapped sample is relatively precisely known, good accuracy of the sample concentration may be obtained. Serial dilutions are also possible by repeating the above steps several times to get successively weaker concentrations.

Control logic 78 supplies control signals to all valves and the pump 70 via control bus 80. The control logic 78 may be a programmed digital computer, dedicated combinatorial logic or any other circuit which can cause the above identified algorithm to work. The details of such logic will be apparent to those skilled in the art given the above description of how the system is supposed to operate, and no further details will be given here.

Although the invention has been described in terms of the preferred embodiment and alternative embodiments disclosed herein, those skilled in the art will appreciate other embodiments which accomplish the same result and which do not depart from the spirit of the invention. All such alternative embodiments are intended to be included within the scope of the claims appended hereto.

What is claimed is:

1. A sample metering valve system for accurately diluting sample having entrapped gas bubbles comprising:

first means for pumping precisely controlled, user defined amounts of sample liquids alternatively into and out of a first system port, said first system port for selective coupling either to a waste receptacle or to a source of diluent or to a source of solvent at different predetermined times;
   second means for supplying pressurized gas into a second system port;
   a container for storing sample or diluted sample;
   valve means for allowing said pumping means to pump sample out of said container into a sample chamber which may be selectively coupled at predetermined times to either said first or said second system ports and for allowing sample in said sample chamber to be isolated from said container and both said ports and for allowing sample in said sample chamber to be placed back into said container and having control inputs for controlling which of the states said valve means is in; and
   control means coupled to said control inputs and to said first and second means for causing said valve means, said first means and said second means to operate in a predetermined sequence to isolate a known amount of sample in said sample chamber and to remove all the remaining sample from said valve means and from said container and to wash said valve means and said container after said removing operation with a solvent and to cause the sample so isolated to have any gas bubbles which may be entrapped therein to be compressed prior to isolation of said known amount of sample, and for pumping said isolated known amount of sample, plus a programmable amount of diluent liquid back into said container.

2. The system of claim 1 wherein said valve means includes first, second and third two-way valves each of which has a common port and first and second switchable ports which are selectively, alternatively coupled to said common port wherein the common port of said first valve is coupled to and in fluid communication with said container and the first and second ports of which are coupled, respectively, to the first and second ports of said second valve, the common port of said second valve being coupled to the common port of said third valve and said third valve having its first port coupled to said first system port and having its second port coupled to said second system port.

3. The system of claim 2 wherein said means for supplying pressurized gas is a source of pressurized nitrogen.

* * * * *